US005560936A

United States Patent [19]

Kador et al.

[11] Patent Number: 5,560,936
[45] Date of Patent: Oct. 1, 1996

[54] INTRINSIC INHIBITORS OF ALDOSE REDUCTASE

[75] Inventors: Peter F. Kador, Potomac, Md.; Yukio Takahashi, Kyoto; Tomoyuki Terada, Osaka, both of Japan; Libaniel Rodriguez, Elkridge, Md.; Matteo Schaffhauser, Bern, Switzerland

[73] Assignee: The United States of America as represented by the Department of Health and Human Services, Washington, D.C.

[21] Appl. No.: 143,203

[22] Filed: Oct. 26, 1993

Related U.S. Application Data

[63] Continuation-in-part of Ser. No. 966,970, Oct. 26, 1992, abandoned.

[51] Int. Cl.$^6$ .......................... A61K 35/23; A61K 35/55; A61K 35/44; C12N 9/04; C12N 9/99
[52] U.S. Cl. .......................... 424/558; 424/568; 424/571; 435/184; 435/190
[58] Field of Search .................................. 435/190, 184; 424/558, 571, 568

[56] References Cited

U.S. PATENT DOCUMENTS

| | | | |
|---|---|---|---|
| 4,382,887 | 5/1983 | Shibata | 424/558 |
| 5,066,676 | 11/1991 | Caccia et al. | 514/562 |
| 5,153,211 | 10/1992 | York | 514/369 |
| 5,155,259 | 10/1992 | Suzuki et al. | 562/469 |

FOREIGN PATENT DOCUMENTS

| | | | |
|---|---|---|---|
| 1013019 | 1/1989 | Japan | 435/184 |
| 1121221 | 5/1989 | Japan | 435/184 |
| 2225485 | 9/1990 | Japan | 435/184 |

OTHER PUBLICATIONS

Akagi, et al., Abst. 6th Cong., VIII–P4 (1991).
Murai, et al., Abst. 6th Cong., VIII–T9 (1991).
Nishigori, et al., *Life Sciences* 45:7 593–598 (1989).
Notsu, et al., Abst. C4.5, Intl. Workshop (1987).
Fukushi, et al., Abst. C4.6, Intl. Workshop (1987).
Sato, et al., *Biochemical Pharmacology*, 40(5) 1033–1042 (1990).
Ohta, et al., *Chem, Phar. Bull.*, 38(6), 1639–1643 (1990).
Reddy, et al., *J. Ocul. Pharmacol.*, 8(1), 43–52 (1992).
Smar, et al., *J. Med. Chem.*, 35(6), 1117–1120 (1992).
Kador, *Int. Congr. Ser.–Excerpts Med.*, 913, 73–79 (1990).
Kador, et al., *Prog. Clin. Biol. Res.* (Enzymol. Mol. Biol. Carbonyl. Metab. 2), 290, 237–250 (1989).
Beyer-Mears, et al., *Pharmacology*, 45(5), 285–291 (1992).
Mylari, et al., *J. Med. Chem.*, 34(3), 1011–1018 (1991).
58 *Fed. Reg.*, 19655 (Apr. 15, 1993).
Kador, et al., *Chemical Abstracts*, 118(25), 439, 21 Jun. 1993.
Eisenthal et al. (1974) *Biochem. J.*, 139, 715–720.
Cornish-Bowden et al. (1974) *Biochem. J.*, *139*, 721–730.
Segel (1975) *Enzyme Kinetics, Behavior and Analysis of Rapid Equilibrium and Steady State Enzyme Systems*, Wiley–Interscience, New York, pp. 170–202.
Robyt et al. (1987) *Biochemical Techniques, Theory and Practice*, Brooks/Cole Publishing, Monterey, pp. 227–230.
Cheronis et al. (1957) *Semimicro Qualitative Organic Analysis, The Systematic Identification of Organic Compounds*, InterScience Publishers, New York, pp. 262–264.

*Primary Examiner*—Michael G. Wityshyn
*Assistant Examiner*—Jon P. Weber
*Attorney, Agent, or Firm*—Townsend & Townsend & Crew LLP

[57] ABSTRACT

An intrinsic aldose reductase inhibitor is isolated and purified from mammalian cells, such as rat or human kidney cells. The intrinsic aldose reductase inhibitor may be incorporated into pharmaceutical compositions for the treatment of certain conditions related to diabetes.

5 Claims, 9 Drawing Sheets

- WITH INHIBITOR
○ WITHOUT INHIBITORS
— 0.030+0.003X
= 0.045+0.004X

Fraction    14 15 23 24 45 crude

INTRINSIC INHIBITORS OF ALDOSE REDUCTASE

This application is a continuation-in-part of Ser. No. 07/966,970, filed Oct. 26, 1992, now abandoned, which is incorporated herein by reference.

BACKGROUND OF THE INVENTION

The present invention relates generally to the isolation, production, and use of enzyme inhibitors. More particularly, the present invention relates to an intrinsic aldose reductase inhibitor (IARI) isolated and purified from mammalian cells.

Aldose reductase is an enzyme (designated EC 1.1.1.21) which catalyzes the conversion of glucose to sorbitol and which is involved in the pathogenesis of certain diabetic complications. In particular, the excess production of sorbitol has been linked with cataracts, retinopathy, keratopathy, neuropathy, myopathy, and nephropathy, and the like. For sometime, the use of aldose reductase inhibitors has been proposed for the treatment of such diabetic complications, and a number of potential therapeutic aldose reductase inhibitors have been identified. Oxazopyrroloquinolone (OPQ), for example, has been used in the treatment of rat sugar cataracts (Terubayashi et al. Abstract, The Sixth Congress of the U.S.—Japan Cooperative Cataract Research Group, Nov. 30–Dec. 5, 1991, Kona, Hawaii, page 200 (1991). Similarly, Nishigori, et al. Life Sciences, 45: 593–598 (1989) describe the treatment of induced cataracts in chicks with pyrroloquinoline quinone (PQQ).

While mostly synthetic compounds, several of the aldose reductase inhibitors are natural products, including pyrroloquinoline quinone (PQQ), a nucleotide analog found in some plants and mammalian tissues, OPQ, a derivative of pyrroloquinoline quinone, certain flavanoids derived from plants, and certain propionic acids derived from microbial sources. For example, Murai et al., Abstract, The Sixth Congress of the U.S.—Japan Cooperative Cataract Research Group, Nov. 30–Dec. 5, 1991, Kona, Hawaii, page 190 (1991), describes a number of aldose reductase inhibitors of microbial origin. Notsu et al. *Abstract C4.5, International Workshop on Aldose Reductase Inhibitors*, Dec. 7–10, 1987, Honolulu, Hawaii (1987) and Fukushi et al. Abstract C4.6, Ibid. describe FR74366 ([3-(4'-bromo-2'fluorobenzyl-7-chloro-2,4dioxo-1,2,3,4-tetrahydro-quinazolin-1yl]acetic acid) and PQQ as aldose reductase inhibitors, respectively.

These aldose reductase inhibitors have proven at least somewhat effective, and in some cases have reached clinical trials. (See Current concepts of aldose reductase and its inhibitions. Sakamoto, et al. eds. Elsevier Science Pub. Inc. New York (1990) p 73–79 for mention of clinical trials and p 129–135 which describes animal (canine) studies) However, most or all of them have displayed side effects and/or toxicity in certain patients. Id.

Thus, it is desirable to identify additional, aldose reductase inhibitors which may be incorporated into therapeutic compositions for use in the treatment of diabetic complications. Such aldose reductase inhibitors should preferably be derived from mammalian sources, more preferably being naturally occurring intracellular substances, particularly polypeptides and polypeptide-like substances, which display an intrinsic aldose reductase inhibition activity.

The present invention provides such aldose reductase inhibitors, which are derived from mammalian cells.

SUMMARY OF THE INVENTION

The present invention provides for intrinsic aldose reductase inhibitors isolated and purified from mammalian cells.

The inhibitors may be purified to provide at least 75% inhibition when assayed by measuring the decrease in the 340 nanometer (nm) absorbance of NADPH in the presence of glyceraldehyde and aldose reductase. The inhibitors further stain ninhydrin positive and have a molecular weight less than 1000. In addition the purified intrinsic aldose reductase inhibitors of the present invention also stain anisaldehyhde positive, 2'–7' dichlorofluorescein negative, fluorescein negative, bromcresol green negative, antimony trichloride ($SbCl_3$) in chloroform ($CHCl_3$) negative, 2,4-dinitrophenyl hydrazine negative, ferric chloride ($FeCl_3$) with 1% added silver (Ag) negative and Dragendorff's reagent negative.

Protein fractions containing the intrinsic aldose reductase inhibitors can be obtained by conventional protein separation techniques. Separated fractions may be assayed, for intrinsic aldose reductase inhibitor activity by measuring the decrease in the 340 nm absorbance of NADPH in the presence of glyceraldehyde and aldose reductase. Fractions exhibiting inhibitor activity may be further purified. For example, the intrinsic inhibitors may be fractionated from the released proteins by ion exchange chromatography, optionally followed by gel chromatography. In this way, aldose reductase inhibitor fractions having a purity of 10% w/w (weight/weight), or higher may be obtained. Compositions having even higher purities may be obtained by further separation.

The intrinsic aldose reductase inhibitors may also be obtained using high performance liquid chromatography. The inhibitors are obtained in an activity peak which fractionates at about 4% methanol in water on a C-18 reverse phase column run in a linear gradient from 2.5% methanol to 50% methanol over 25 minutes. The inhibitors can be further purified so as to appear in a single activity peak when the intrinsic aldose reductase-containing fractions obtained from the C-18 reverse phase column are pooled and run isocratically on a C-8 column in 2.5% methanol.

The invention further comprises a method for inhibiting aldose reductase activity in a cell by administering an intrinsic aldose reductase inhibitor to that cell, where inhibitor is itself isolated and purified from mammalian cells. The cell may be a mammalian cell, in particular a cultured human cell.

The invention also provides a method of purifying intrinsic aldose reductase inhibitors from mammalian cells. The method comprises the steps of:

[a] extracting and concentrating intracellular materials from the mammalian cells;

[b] fractionating the materials based on physical or biological characteristics and collecting fractions;

[c] assaying the fractions for aldose reductase inhibition activity;

[d] collecting and pooling those fractions having aldose reductase inhibition activity; and

[e] repeating steps [b] through [d] from 1 to 5 times.

The extraction and concentration of intracellular materials may be accomplished by homogenizing a mammalian tissue, in particular human or mouse kidney, in ethanol to form a homogenate; centrifuging the homogenate to produce a supernatant; filtering the supernatant; and then concentrating the supernatant to dryness by evaporation.

Fractionating the materials may be accomplished by high performance liquid chromatography (HPLC) using a reverse phase C-18 column and a buffer system of water for solvent A and 50% methanol for solvent B and collecting the fractions containing the activity peak that elutes at about a 4% methanol concentration. The aldose reductase inhibitors may then be further fractionated by pooling the fractions containing the activity peak and further purifying them by high performance liquid chromatography using a C-8 column run isocratically in 2.5% methanol in water and collecting the fractions comprising the single predominant activity peak.

Assaying the fractions for aldose reductase inhibition activity may be accomplished by measuring the decrease in the 340 nm absorbance of NADPH in the presence of glyceraldehyde and aldose reductase.

The intrinsic aldose reductase inhibitor compositions may be used for inhibiting aldose reductase activity in cells either in vivo or in vitro. The cells may be mammalian cells and, in particular, may be cultured human or rat cells. The intrinsic aldose reductase inhibitor compositions may also be incorporated into pharmaceutical compositions for in vivo use.

GENERAL DESCRIPTION DEFINITIONS

The term "mean activity" as used herein refers to the average rate of reaction of an aldose reductase determined from two or more experimental measurements. Activity is determined by detecting the rate of conversion of NADPH to $NADP^+$ in the presence of aldose reductase and an appropriate substrate. NADPH conversion may be measured by the decrease in absorbance of the sample at 340 nm. This may be done by running the assay in a spectrophotometer. Mean activity is expressed as nanomoles/minute/milliliter (nmols/min/ml) NADPH consumed.

The term "percent remaining activity" as used herein refers to the activity or mean activity of an inhibitor-treated enzyme source (e.g. aldose reductase exposed to an IARI)

compared to an untreated enzyme source, expressed as a percentage of activity remaining after treatment; "No treatment" is 100% remaining activity while complete inhibition is 0% remaining activity. Percent remaining activity is calculated by taking the ratio of the inhibitor treated enzyme to the untreated enzyme and multiplying by 100.

The term "percent inhibition" as used herein refers to the percentage of inhibition of aldose reductase activity produced by an intrinsic aldose reductase inhibitor. Percent inhibition is calculated as the difference between 100% and the percent remaining activity.

The term "intrinsic aldose reductase inhibitor(s)", designated IARI, refers to substances that are produced within mammalian cells and function intracellularly to inhibit the aldose reductase-catalyzed conversion of glucose to sorbitol.

The term "stains [indicator name] positive" as used herein refers to the binding or chemical reaction of a particular indicator with, the compound being tested. The indicator, when bound or reacted, may be visualized to determine its presence or chemical reaction with the tested compound. Indicator compounds are selected which bind to or react with characteristic chemical groups. Thus the indicator may be used to determine the presence of particular chemical groups in the tested composition. For example, a composition that stains ninhydrin positive binds, and indicates the presence of, amino acids, amino sugars, or phosphatides. Other indicators include 2'7' dichlorofluorescein for lipids and lipophiles, fluorescein for conjugated systems, bromcresol green for carboxylic acids, $SbCl_3$ in $CHCl_3$ for steroids, vitamins, lipids and cartenoids, 2,4-dinitrophenyl hydrazine for aldehydes and ketones, $FeCl_3$ (1% Ag) for phenols and enols, and Dragendorff's reagent for alkaloids and organic bases.

In contrast, the term "staining negative" refers to the situation where a particular indicator shows no specific binding. This is generally revealed by a degree of staining indistinguishable from the generalized background staining of the medium in which the test compounds are suspended.

Figure 13:
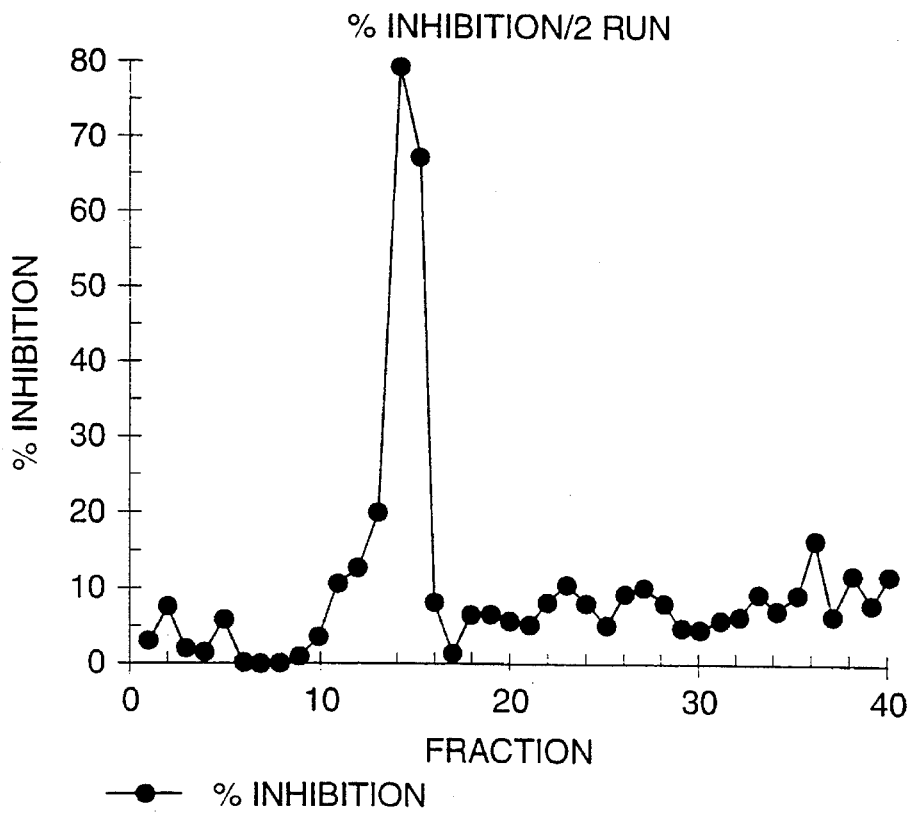
FIG. 13 represents an HPLC run on the collected void volume (fractions 6–8 in FIG. 12) of the C-18 column conducted on a C-8 column (pH stable RP C-8 column, 90 Å, 9×250 mm, Vydak, Hesperia, Calif.) run isocratic in water containing 2.5% methanol at a rate of 0.3 ml/min collecting fractions at 0.3 minute intervals.

The term "activity peak" refers to a portion of an elution profile whose fractions contain enhanced aldose reductase inhibitor activity as compared to other fractions in the elution profile. When inhibitor activity is plotted as a function of fraction number, an activity peak appears as a hump or local peak in the profile. Activity peaks may be broad when the inhibitory activity is distributed over a large number of fractions produced by a particular separation method. Alternatively an activity peak may be quite narrow and fully contained within a single fraction. FIG. 13, for example illustrates a narrow activity peak contained essentially within two fractions (fractions 14 and 15).

The phrase "purified and isolated" refers to material that is substantially or essentially free from components which normally accompany it as found in its native state. Thus a naturally occurring protein which is removed from the cell and the majority of other proteins present in the cell (e.g. through standard protein purification techniques) thereby increasing its concentration and activity may be said to be purified and isolated.

A "pharmaceutically acceptable carrier" refers to a carrier medium which does not interfere with the effectiveness of the aldose reductase inhibitor and which is non-toxic to the hosts to which it is administered. Such carriers may include, but are not limited to sterile water, buffer solutions, alcohol, fats, waxes and inert solids.

DETAILED DESCRIPTION OF THE INVENTION

The present invention provides for compositions comprising isolated or purified intrinsic aldose reductase inhibitors (IARIs). These intrinsic aldose reductase inhibitors are naturally occurring compounds which have aldose reductase inhibition activity and which are isolated or otherwise derived from mammalian cells. By "intrinsic," it is meant that these substances are produced within the mammalian cells and function intracellularly to inhibit the aldose reductase-catalyzed conversion of glucose to sorbitol.

The intrinsic aldose reductase inhibitor compositions of the present invention will comprise at least a single compound or a planned combination of one or more inhibitors which either singly or in combination display aldose reductase inhibition activity. In particular, it is presently believed that the compositions of the present invention will often comprise three or more substances, at least two of which will be polypeptides or proteins (which demonstrate positive ninhydrin staining) and which together or separately display aldose reductase inhibition activity.

In general the process of isolating the aldose reductase inhibitors comprises extracting the compounds from mammalian tissue source. After initial isolation of the compounds from large cellular components, the aldose reductase inhibitors may be isolated and purified by conventional protein purification techniques such as clarification, concentration, and chromatography. Separated fractions may be assayed to determine those containing enhanced inhibition activity. The fractions containing activity may be further purified. The purified aldose reductase inhibitors may then be characterized by measurement of their physical properties and inhibitory activity.

Extraction of Aldose Reductase Inhibitors from Mammalian Tissues

The intrinsic aldose reductase inhibitors will be purified or otherwise obtained from mammalian cells. The cells may be derived from any mammal including, for example, cats, dogs, mice, humans, monkeys, etc. Particular sources of cells include tissue cells, tissue cell lines, and the like. Preferred are cellular sources having significant levels of aldose reductase activity, such as kidney cells, lens cells, thyroid cells, and the like.

The cells of the cellular source will be disrupted, either physically or chemically, to release the intracellular materials. Methods of disrupting cells are well known to those of skill in the art. For example mechanical means of disrupting cells include, but are not limited to, homogenization, as with a blender, or sonication. Chemical means include, but are not limited to, treatment with detergents, such as SDS, or placement of the cells in hypotonic media. Methods preparation of crude cellular homogenates are well known to those of skill in the art. For example, see Deutscher, M. P. *Methods in Enzymology Vol.* 182: Guide to Protein Purification, Academic Press, Inc. New York (1990).

Preliminary isolation or concentration of the intrinsic aldose reductase may be performed by a number of means known to those of skill in the art. The separation of gross cellular components may be accomplished by filtration, centrifugation, and the like. Preliminary concentration may be accomplished by means including, but not limited to dialysis, lyophilization and evaporation. One of skill would recognize that these means may be used in combination with each other and various steps of concentration may be repeated through a number of iterations.

In one embodiment of the present invention, extraction may be performed by homogenizing the source tissue with water in a blender. The homogenate is then centrifuged at 10,000 rpm (12,000×g) for 60 minutes. The resultant supernatant is applied to a Sephadex G-50 gel filtration column (2.4×71 cm) and the sample is eluted with water at a flow rate of 2.25 milliliter (ml)/minute. The fractions are then evaluated for aldose reductase inhibitory activity as described below. Those fractions showing activity are collected and pooled.

The preferred method of extraction, however, is accomplished by homogenizing the source tissue in a blender using 2 ml of ethanol per gram of tissue. The homogenate is centrifuged at 8000 rpm (10810×G) for 45 minutes and the supernatant is then filtered through glasswool. The supernatant is then concentrated to dryness by evaporation in a Rotavapor-R (Buechi) and redissolved in 20 ml of water yielding a solution with a yellowish color.

Assaying for Aldose Reductase Inhibitor Activity

In order to determine which fractions from a particular separation contain the concentrated aldose reductase inhibitors, an assay is required to detect the presence or absence of the aldose reductase inhibitor. One of skill would recognize that such assays may take many forms depending on the particular physical and chemical properties of the aldose reductase inhibitors. Examples of assays include, but are not limited to stains specific to the IARI, or particular spectroscopic absorption profiles and the like.

In a preferred embodiment, one may assay for aldose reductase inhibitors by measuring the presence or absence of actual aldose reductase inhibitory activity. Aldose reductase inhibitory activity may be measured by determining the rate of reduction of a particular substrate by aldose reductase without the presence of an inhibitor. This provides a control for comparison to the rate of reduction of a particular substrate in the presence of a possible aldose reductase inhibitor. Intrinsic aldose reductase inhibitor activity may be expressed as percent remaining activity (of the reductase) or as percent inhibition. Percent remaining activity is calculated by taking the ratio of the inhibitor treated enzyme to the untreated enzyme and multiplying by 100. One hundred percent minus the percentage remaining activity gives the percentage inhibition.

The rate of reaction of aldose reductase may be determined photometrically, detecting the rate of conversion of NADPH to $NADP^+$ by measuring the decrease in absorbance of the sample at 340 nm. This is most easily accomplished by running the reaction in a spectrophotometer.

One of skill would recognize that the assay may be run using a number of substrates including, but not limited to glyceraldehyde, glucose, or 3-fluoro-3-deoxy-D-glucose (3FDG). In a preferred embodiment, the substrate will be DL-glyceraldehyde. Photometric assays for aldose reductase are well known to those of skill in the art. Protocols may be found, for example in Hyman & Kinoshita, *J. Biol. Chem.* 240: 877 (1965), Ohta et al. *Chem. Phar. Bull.* 38: 1639–1643 (1990) and Kador et al. *Anal. Biochem.* 114: 53–58 (1981).

In another embodiment, the aldose reductase inhibitors may be assayed by using nuclear magnetic resonance (NMR) to detect the reduction of the substrate directly as in Example 1.

Aldose reductase for use in the assays and as a control may be obtained by partial purification, using Sephadex G-75, of homogenates of mammalian lens tissue. Methods of isolation of aldose reductase may be found in Kador et al. Anal. Biochem. 114: 53–58 (1981), Shiono et al. *Progr. Clin. Biol. Res.* 232: 317–324 (1987) and in Ohta et al. *Chem. Phar. Bull.* 38: 1639–1643 (1990).

Purification of Aldose Reductase Inhibitors from Mammalian

The intrinsic aldose reductase inhibitors may be purified by conventional protein purification techniques. These include precipitation, chromatographic techniques, such as ion exchange chromatography, size exclusion chromatography (such as Sephadex gel chromatography), hydrophobic chromatography, reverse-phase chromatography, affinity chromatography, silica gel chromatography, high performance liquid chromatography (HPLC) and the like. Techniques of protein purification are well known to those of skill in the art (See, for example Deutscher, M. P. *Methods in Enzymology Vol.* 182: *Guide to Protein Purification*, Academic Press, Inc. New York (1990)).

Usually, two or more separate protein purification steps will be sequentially performed in order to achieve a desired level of purification. Conveniently, the various fractions produced by each purification step can be assayed, as described above, to detect intrinsic aldose reductase inhibition activity, and those fractions collected and utilized, or optionally, subjected to additional purification steps.

Figure 2:
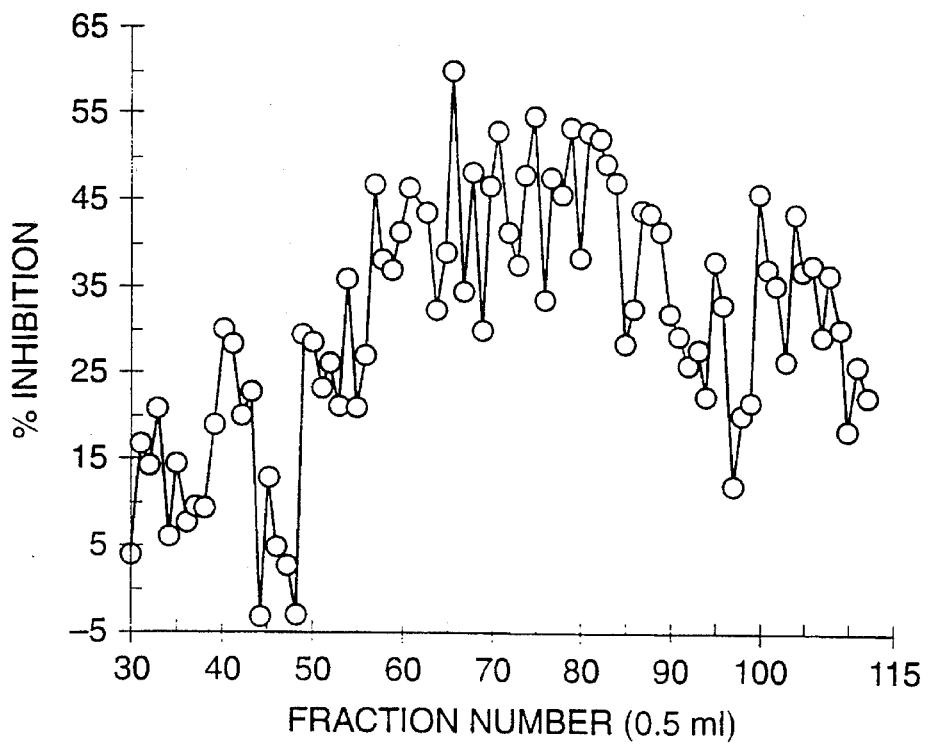
FIG. 2 is an elution profile showing the results of purification of the pooled IARI-containing fractions from the G-50 column (FIG. 1) by silica gel column chromatography. Chromatography was performed using a 2.0×20 cm column (Merck grade 60, 230–400 mesh 60 Å, Sigma, St. Louis, Mo.) with an acetonitrile:water:TFA (90:10:0.5) v/v (volume/volume) solvent system. Two peaks containing intrinsic aldose reductase inhibitor (IARI) activity were obtained. The first, a broad peak, corresponded to fractions 50 to 95. The second, narrower peak, corresponded to fractions 100 to 115.

A significant level of purification can be obtained by ion exchange chromatography followed by silica gel chromatography. For example, the aldose reductase inhibitor containing composition extracted as described above may be further fractionated using a 2.5×55 centimeter (cm) CM-52 cellulose cation exchange column (Sigma, St. Louis, Mo.). The fractions containing aldose reductase inhibitory activity are then collected pooled and lyophilized. The lyophilized material is then redissolved in water, applied to a 2.0×20 cm column containing silica gel (Merck grade 60, 230–400 mesh 60 Å, Sigma, St. Louis, Mo.), and eluted with an acetonitrile:water:trifluoroacetic acid (TFA) (90:10:0.5 v/v) solvent system. This produces two peaks containing intrinsic aldose reductase inhibitory activity as illustrated in the elution profile from the silica gel column shown in FIG. 2.

Figure 3:
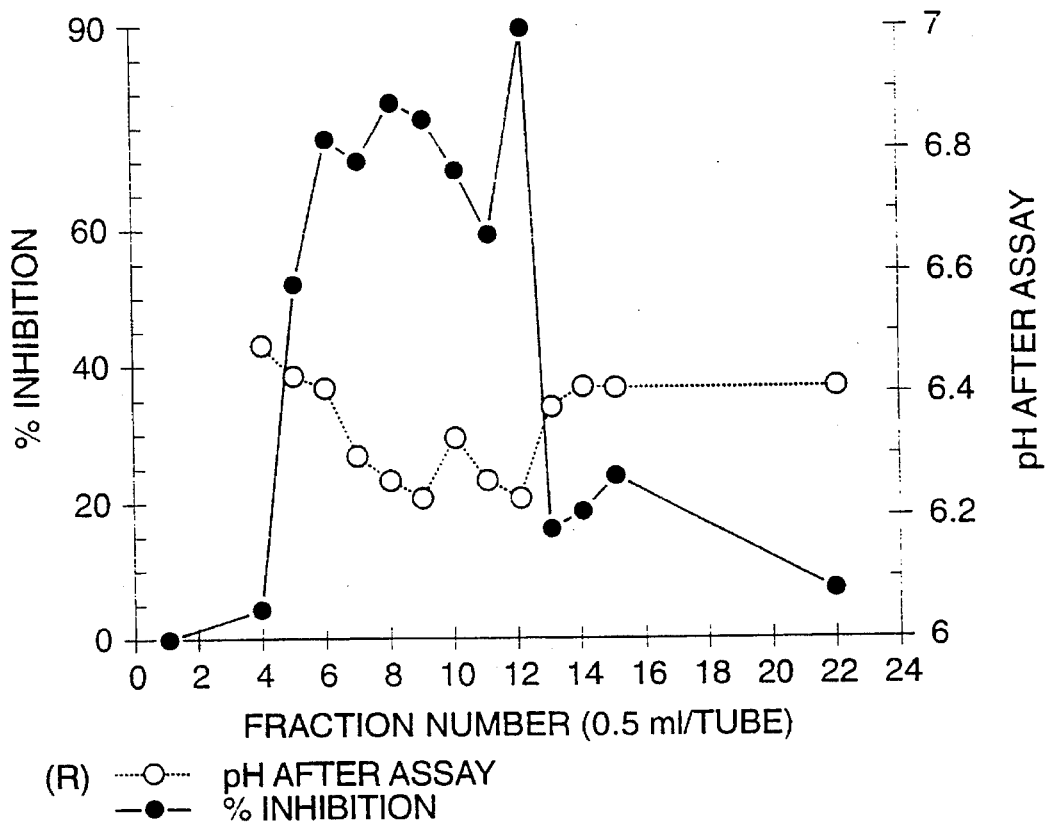
FIG. 3 is an elution profile showing the results of purification of the pooled IARI-containing fractions from the G-50 column (FIG. 1) by flash chromatography on a 2.0×5 CM silica gel column (Merck grade 60, 230–400 mesh 60 Å, Sigma, St. Louis, Mo.) using an acetonitrile:water:TFA (50:50:0.5 v/v) solvent system. Intrinsic aldose reductase inhibitor activity was found in one broad peak, corresponding to fractions 5 through 10, and another sharp peak, found in fraction 12.

Alternatively, the fractions containing intrinsic aldose reductase inhibitory activity obtained from ion exchange chromatography may be further purified by flash chromatography on a silica gel column. The fractions after being pooled, lyophilized and resuspended in water are applied to a silica gel column (2.0×5 cm) using an acetonitrile:water:TFA (50:50:0.5 v/v) solvent system. This produces an elution profile as illustrated in FIG. 3.

A preferred purification method that produces good separations with highly reproducible results is reverse phase high performance liquid chromatography (HPLC). The intrinsic aldose reductase inhibitor containing tissue is extracted according to the preferred method described above and then fractionated using reverse phase HPLC on a C-18 column (RP C-18 90 Å pharmaceutical column, 9×250 mm, Vydac, Hesperia, Calif.). In this HPLC system, solvent A is water and solvent B is 50% methanol. The separation is performed using a gradient that provides a 10 minute equilibration at 2.5% methanol followed by a 25 minute linear gradient going from 2.5% to 50% methanol.

Figure 12:
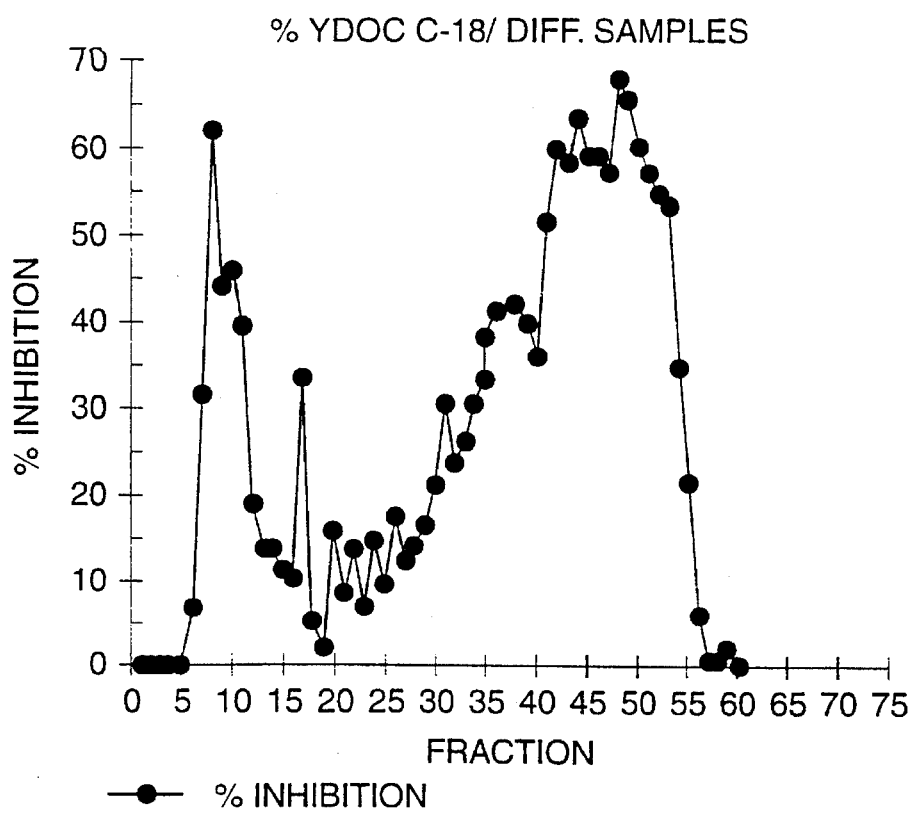
FIG. 12 represents an HPLC of human kidney extract run on a C-18 column (RP C-18 90 Å pharmaceutical column, 9×250 mm, Vydac, Hesperia, Calif.) using an LKB HPLC system. In this system, solvent A was water and solvent B was 50% methanol in water. The column was equilibrated for the first 10 minutes with a starting buffer of 2.5% methanol-water. Between 10–35 minutes a linear gradient (25 minutes long) was run to a final buffer concentration of 50% methanol. The flow rate was 1.5 ml/min with fractions collected at 1 minute intervals.

HPLC using this protocol provides highly consistent elution profiles containing characteristic peaks at about 4% methanol and 50% methanol as shown in FIG. 12. The peak eluting at about 4% methanol actually corresponds to the void volume of the C-18 column. The fractions corresponding to this peak may be collected, pooled, and fractionated again using a C-8 column (pH stable RP C-8 column, 90 Å, 9×250 mm, Vydak, Hesperia, Calif.) run isocratic in water containing 2.5% methanol. The elution profile of the C-8 column, shown in FIG. 13, reveals a profile with a characteristic single dominant peak. Fractions selected from this peak show aldose reductase inhibitory activity in excess of 75%.

One of skill would recognize that the selection of fractions from a particular elution profile is a function of the amount of purified material desired, the degree of purity desired, and the subsequent use of the material. The selection of fractions is routine to one of skill in the art. In general, there is a trade-off between the amount of the composition obtained and its purity. One maximizes purity by selecting fractions from the elution profile showing maximum activity. Typically only one or two fractions contain material from the apex of a particular activity peak. Selecting more fractions produces more material, but the purity is reduced. If there are fewer or no subsequent purification steps, one would select fewer fractions taking the higher purity material close to the apex of a peak. Where there are more subsequent purification steps one generally selects more fractions to provide more of the material of interest relying on the subsequent purification steps to provide greater purity. Where there is a need for greater quantity and higher purity one may start with larger amounts of material and perform the purification steps with higher capacity columns.

The intrinsic aldose reductase inhibitor(s) of the present invention are obtained in at least partially purified form, typically being at least about 10% weight/weight (w/w) pure and being free from contaminants and substances which interfere with the desired inhibition activity. Usually, the intrinsic aldose reductase inhibitor compositions are at least 25% w/w pure, more usually being at least 50% w/w pure, and preferably being at least 75% w/w pure, or higher. In many cases substantially pure compositions of the aldose reductase inhibitor of the present invention, typically being greater than 90% w/w pure, preferably being greater than 95% w/w pure, and sometimes being 99% w/w pure or higher are obtained. Compositions having such high purity can be obtained using the protein purification techniques described above.

The intrinsic aldose reductase inhibitors of the present invention show at least 2.5% inhibition, more usually at least 50% inhibitory activity and preferably at least 75% inhibitory activity. Where substantially pure compositions of the present are obtained they show greater than 90% inhibitory activity.

Characterization of Aldose Reductase Inhibitors

The intrinsic aldose reductase inhibitors of the present invention have a molecular weight of less than 1000 as indicated by FAB mass spectrometry and the fact that they pass through a dialysis membrane with a molecular weight cutoff of 1000. The inhibitors are heat stable and may be subjected to a temperature of 100° C. for 60 minutes without a significant loss of inhibitory activity. Trypsin, chymotrypsin, pronase K or pronase E, have little effect on inhibitory activity of intrinsic aldose reductase inhibitors, but exposure to high concentrations of acids or bases does decrease the inhibitory activity. Finally the intrinsic aldose reductase inhibitors of the present invention absorb at UV254 and bind ninhydrin indicating a peptide component.

Uses of Intrinsic Aldose Reductase Inhibitors

Mounting experimental evidence indicates that the NADPH-dependent reduction of glucose to the sugar alcohol sorbitol, catalyzed by aldose reductase, provides a common link in the onset of long-term diabetic complications that result in tissue and/or functional changes in the cornea, lens, retina, iris, peripheral nerves and kidney. Kador Med. Res. Rev. 8: 325–352 (1988), Kador et al. *Arch. Ophthalmol.* 106: 1099–1102 (1988). In addition, pharmacological studies indicate that the onset and progression of these complications can be prevented or reduced significantly by the inhibition of sugar alcohol formation. Dvornik, *Aldose reductase Inhibition,* D. Porte, ed. Biomed. Info. Corp. (1987), pp 73–88, 326–349, Kador, Med. Res. Rev. 8: 325–352 (1988), Kador et al. *Arch. Ophthalmol.* 106: 1099–1102 (1988).

The intrinsic aldose reductase inhibitors of the present invention may be used to inhibit aldose reductase activity in vivo or in vitro. In vitro inhibition can be used to study aldose reductase activity, particularly as part of studies relating to the diabetic condition. Specifically intrinsic aldose reductase may be used as a component of a diagnostic assay system useful in screening for altered forms of aldose reductase associated with various disease states. For example, changes in the degree of inhibition caused by a fixed concentration of aldose reductase inhibitor would be diagnostic of alterations in the activity of an aldose reductase.

In vivo uses of intrinsic aldose reductase inhibitors include administration of the inhibitors to mammalian hosts, such as human hosts, suffering from aldose reductase-related conditions, particularly diabetic complications as described above. It is expected that the intrinsic aldose reductase inhibitor(s) of the present invention will have reduced side effects, enhanced biocompatibility, and/or improved effectiveness when compared to at least some of the previously known aldose reductase inhibitors.

Pharmacological Compositions Containing Aldose Reductase Inhibitors

The intrinsic aldose reductase inhibitors of the present invention may be incorporated in a pharmaceutically-acceptable carrier to provide pharmaceutical compositions for in vivo therapy. Such pharmaceutical compositions should contain a therapeutic amount of at least one of the intrinsic aldose reductase inhibitor(s), and the pharmaceutically-acceptable carrier can be any compatible, non-toxic substance suitable to deliver the inhibitor(s) to an intended host. Sterile water, alcohol, fats, waxes, and inert solids may be used as the carrier, typically for systemic administration. Pharmaceutically-acceptable adjuvants buffering agents, dispersing agents, and the like, may also be incorporated into the pharmaceutical compositions. Preparation of pharmaceutical compositions incorporating active agents is well described in the medical and scientific literature. See, for example, *Remington's Pharmaceutical Sciences,* Mack Publishing Company, Easton, Penn., 16th ed. (1982).

The pharmaceutical compositions just described are generally suitable for systemic administration to a host, including both parenteral and oral administration. The pharmaceutical compositions may be administered parenterally, i.e., subcutaneously, intramuscularly, or intravenously. Thus, the present invention provides compositions for administration to a host, where the compositions comprise the intrinsic aldose reductase inhibitor present in a pharmaceutically acceptable carrier, as described above.

The concentration of the intrinsic aldose reductase inhibitor in the pharmaceutical carrier may vary widely, i.e., from less than about 0.1% by weight of the pharmaceutical composition to about 20% by weight, or greater. Typical pharmaceutical compositions for intramuscular injection will be made up to contain, for example, 1 to 4 ml of sterile buffered water and 1 microgram (μg) to 1 milligram (mg) of the inhibitor compound.

In therapeutic applications, compositions are administered in an amount sufficient to cure or at least partially alleviate certain signs, symptoms, side effects, or the like, associated with the diabetic condition of a host. These include, for example cataract formation, keratopathy, neuropathy, myopathy, and nephropathy. In particular, aldose reductase inhibitors are of use in the treatment of diabetic retinopathy which is characterized by the formation of microaneurysms, exudates, macular edema and small intraretinal hemorrhages, neovascularization, fibrovascular proliferation and vitreous hemorrhages.

An amount of an intrinsic aldose reductase inhibitor adequate to cure or partially alleviate these or other symptoms associated with the aforementioned diseases is defined as a "therapeutically effective dose." Amounts effective for this use will depend on the severity of the disease and the weight and general state of the patient, but generally range from about 0.1 mg to about 2,000 mg of inhibitor per day for a 70 kg patient, with dosages of from about 0.5 mg to about 1,000 mg of inhibitor per day being more commonly used.

The intrinsic aldose reductase inhibitors of the present invention may also be incorporated in a physiologically acceptable carrier suitable for topical application, particularly for application to the eyes in the treatment of cataracts. Preparation of suitable ophthalmic solutions require careful consideration of factors such as isotonicity, the need for buffering agents, the need for preservatives, and sterilization. Lacrimal fluid is isotonic with physiological fluids, having an isotonicity value corresponding to that of 0.9% sodium chloride. Ideally, an ophthalmic solution should have this isotonicity value, but eyes can tolerate isotonicity values as low as that of a 0.6% sodium chloride solution and as high as that of a 2.0% sodium. chloride solution without substantial discomfort. Some ophthalmic solutions are necessarily hypertonic in order to enhance absorption and provide a concentration of the active inhibitor protein strong enough to exert a prompt and effective action. Suitable ophthalmic carriers include ointments, saline solutions, isotonic saline solutions, such as Sorbi-Care (Allergan Pharmaceuticals, Irvine, Calif.), Neodecadrone (Merck, Sharp, and Dohme, West Point, Pa.), and the like.

The following examples are offered by way of illustration, not by way of limitation.

EXAMPLE 1

Evaluation of Aldose Reductase Inhibitor Activity

Aldose reductase activity was spectrophotometrically assessed by following the decrease in the 340 nm absorbance of NADPH as described in Kador et al. *Anal. Biochem.* 114: 53–58 (1981) and summarized here. Inhibitor effects on aldose reductase activity were measured in cuvettes containing 100 millimolar (mM) phosphate buffer, pH 6.2, 10 mM DL-glyceraldehyde, 0.3 mM β-NADPH, and approximately 3 milliunits (mU) of aldose reductase, in 50 microliters (μl) of inhibitor solution. The assay was initiated by the addition of aldose reductase after all other reagents were added. Control experiments were performed in the absence of the inhibitor.

Aldose reductase for use in the assays and as a control was obtained by partial purification, using Sephadex G-75, of homogenates of mammalian lens tissue according to the method of Hyman and Kinoshita, *J. Biol. Chem.* 240: 877 (1965).

Purification of Intrinsic Aldose Reductase Inhibitor (IARI)

Figure 1:
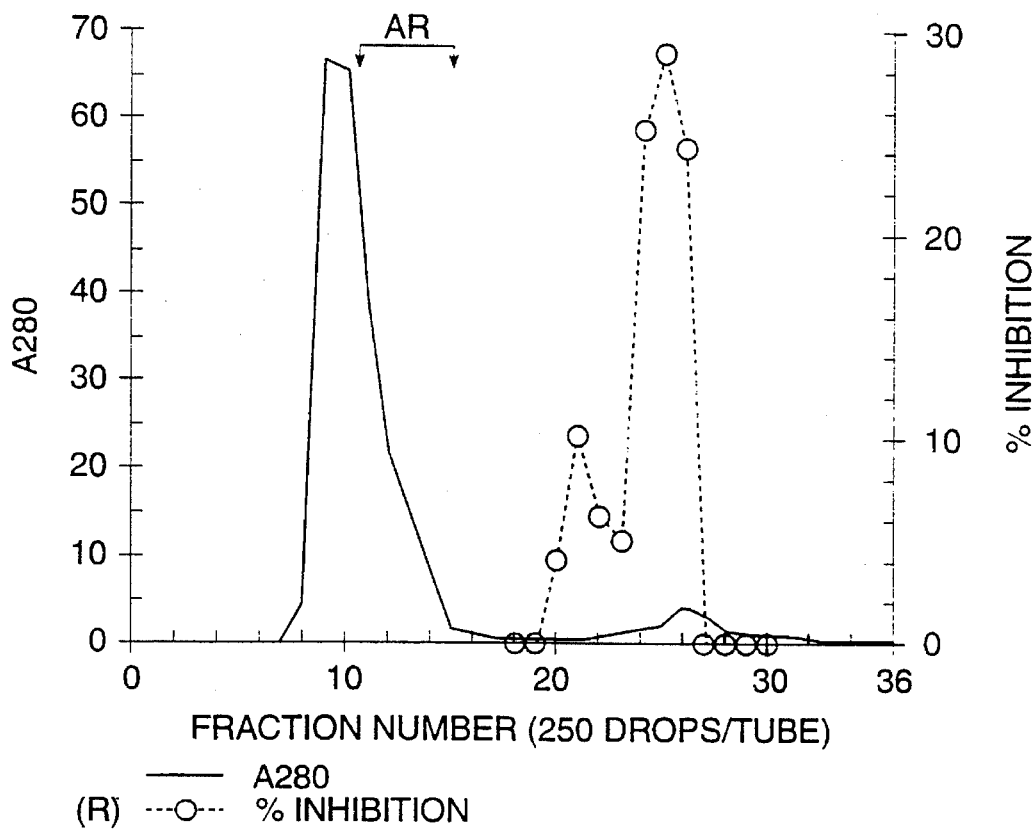
FIG. 1 is an elution profile of material obtained from rat kidney cells which have been separated on a Sephadex G-50 gel filtration column (2.4×71 cm).

Purification of the IARI was performed using gel filtration, ion exchange and flash column chromatography techniques. Inhibitor fractions were evaluated against rat lens aldose reductase partially purified by Sephadex G-75 gel filtration chromatography. The inhibitor purification was conducted as follows:

Twenty rat kidneys (13.7 grams) were homogenized with two volumes of water in a Waring blender, and the homogenate was centrifuged at 10,000 rpm (12,000×g) for 60 minutes. The resultant supernatant was applied to a Sephadex G-50 gel filtration column (2.4×71 cm), and the sample was eluted with water at a flow rate of 2.25 ml/min. The fractions were collected (100 drops/tube i.e., about 4 ml/tube) and each fraction was spectrophotometrically evaluated for protein content (280 nm) and inhibition of aldose reductase. The elution profile shown in FIG. 1 indicates that the IARI eluted in fractions 19–25 while the majority of proteins eluted in fraction 9–15. This indicates that the inhibitor fraction is of a smaller molecular size than most proteins found in the kidney.

Fractions containing the IARI were further purified by CM-52 cation exchange chromatography (2.0×10 cm column). All IARI in the unabsorbed fraction was collected and lyophilized. The lyophilized material containing IARI was then redissolved in water, applied to a 2.0×20 cm column containing silica gel (Merck grade 60, 230–400 mesh 60 Å), and eluted with a acetonitrile:water:TFA (90:10:0.5 v/v) solvent system. Essentially two peaks containing IARI activity were obtained, as illustrated in the elution profile of the IARI on silica gel column chromatography (2.0×20 cm) in FIG. 2. The first peak, corresponding to fractions 50 to 95, was yellow in color while the second, corresponding to fractions 100 to 115, appeared essentially colorless. The two peaks were collected separately, lyophilized, and further purified.

Alternatively, IARI fractions obtained by ion exchange chromatography were subjected to flash chromatography on a 2.0×5 cm silica gel column (Merck grade 60, 230–400 mesh 60 Å, Sigma, St. Louis, Mo.) using an acetonitrile:water:TFA (50:50:0.5 v/v) solvent system as illustrated in FIG. 3. As in FIG. 2, one broad peak, corresponding to fractions 5 through 10, and another sharp peak, found in fraction 12 were obtained.

Figure 4:
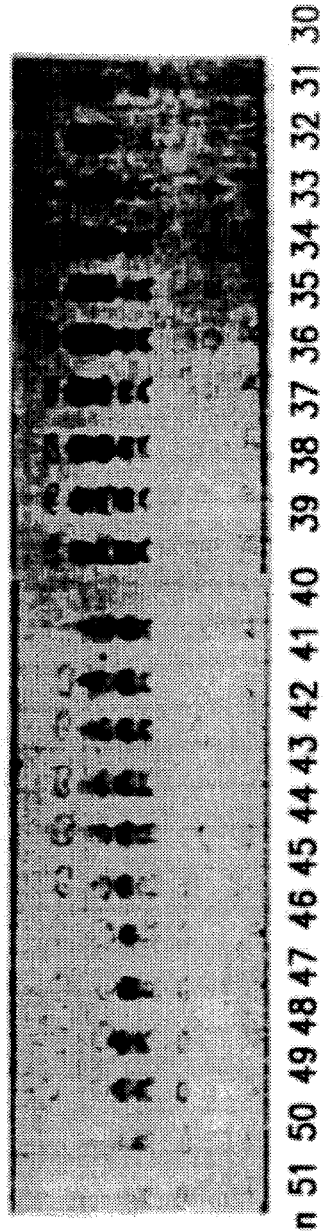
FIG. 4 illustrates the results of thin layer chromatography (TLC) of each fraction produced in a flash chromatography purification as described in FIG. 3. To provide enough material for TLC the chromatography method described in FIG. 3 was scaled up using the same protocol with a 2.0×25.0 cm column. This provided an elution profile similar to that seen in FIG. 3. TLC was performed on each fraction using Whatman, KG silica gel (250 micrometers (μm) thick) and an acetonitrile:water:TFA (70:30:0.5 v/v) solvent system, and strained with ninhydrin.

The flash chromatography separation was scaled up using the same protocol, but replacing the 2.0×5 cm column with a 2.0×25 cm column. Elution profiles obtained with the larger column were similar to FIG. 3. Fractions (0.5 ml) from the flash chromatography system were collected and evaluated by thin layer silica gel chromatography (Whatman, KG silica gel, 250 μm thick, Sigma, St. Louis, Mo.) using a variety of solvent systems. Separations on the TLC plates were initially detected by UV at 254 nm and 365 nm and subsequently visualized with ninhydrin. Solvent was then removed from each fraction, and each dried fraction was resuspended in water and enzymatically evaluated. As illustrated in FIG. 4, a number of spots could be observed with an acetonitrile:water:TFA (70:30:0.5 v/v) solvent system.

Starting from right to left with sample 30, the spots outlined with solid lines (uppermost spots) represent compound(s) that were visualized by fluorescence at 254 nm while those outlined by the dotted lines (two or three spots below the upper spot) were fluorescent at 365 nm. The black spots stained positive with ninhydrin. Both the middle and lower spots appear to weaken from right to left while the upper spots appear to grow stronger from right to left. Poor separations were observed with organic solvents such as hexane, methanol, cyclohexane, ethylacetate and chloroform, suggesting that the IARI is water soluble.

Properties of Intrinsic Aldose Reductase Inhibitor Heat Stability

Figure 5:
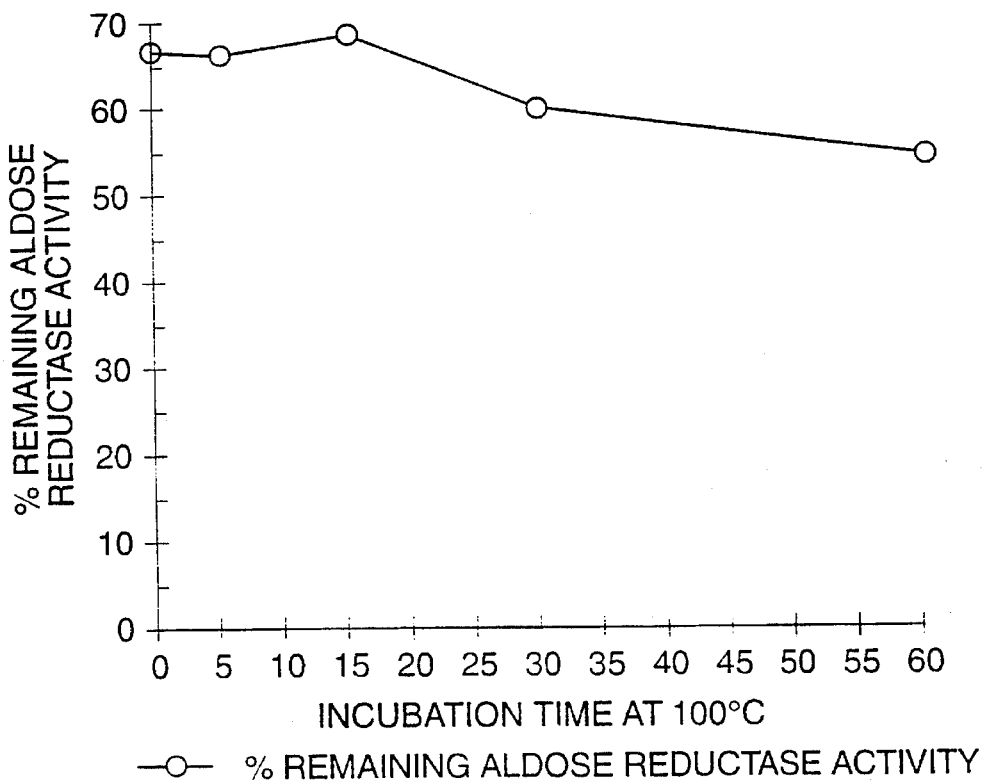
FIG. 5 illustrates the loss in activity of the intrinsic aldose reductase inhibitor of the present invention over the course of 60 minutes when exposed to a temperature of 100° C. The data is presented as the percent remaining aldose reduction activity as a function of heating time.

The IARI appears to be heat stable. Temperatures of 100° for 60 minutes not significantly reducing the IARI's ability to inhibit aldose reductase. The percent remaining activity as a function of time at 100° C. is summarized in FIG. 5.

Stability Toward Proteolysis and Hydrolysis

The ability of the IARI to inhibit aldose reductase was not affected by treatment with trypsin, chymotrypsin, pronase K and pronase E. IARI activity was reduced when the lyophilized IARI was dissolved in either 1M HCl or 1M NaOH. IARI was incubated at 60° C. for 16.5 hr, neutralized, and evaluated for its ability to inhibit aldose reductase. As summarized in Table 1 below, the activity of aldose reductase in the presence of IARI treated with either acid or base was greater than the activity of aldose reductase in the control solution (containing normal IARI). Thus treatment with acid or base diminished the inhibitory activity of IARI.

TABLE 1

The Effect of Acid and Base on the Inhibitory Activity of IARI.

| Treatment | Activity* Exp. 1. | Activity* Exp. 2. | Mean Activity* | % Remaining Activity |
|---|---|---|---|---|
| No IARI | 40.86 | 40.66 | 40.76 | |
| IARI + Water | 8.43 | 8.11 | 8.27 | 20.29 |
| IARI + 1M HCl | 21.56 | 17.06 | 19.31 | 47.37 |
| IARI + 1M NaOH | 14.15 | 15.90 | 15.02 | 36.86 |

*Activity is expressed as nmols/min/ml NADPH consumed.

Mechanism of Inhibition of Aldose Reductase by IARI.

Figure 6:
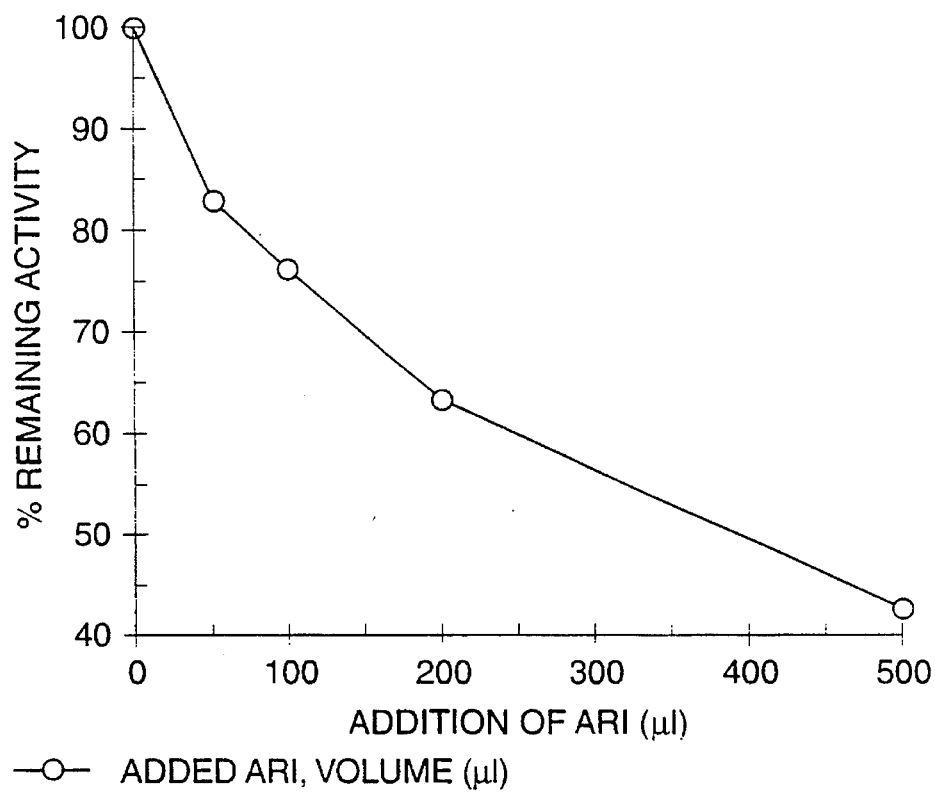
FIG. 6 illustrates the reduction in aldose reductase activity as a function of the amount of added intrinsic aldose reductase inhibitor. The percent remaining activity (of aldose reductase) is plotted as a function of the amount of intrinsic aldose reductase inhibitor (ARI) added to the assay.
Figure 7:
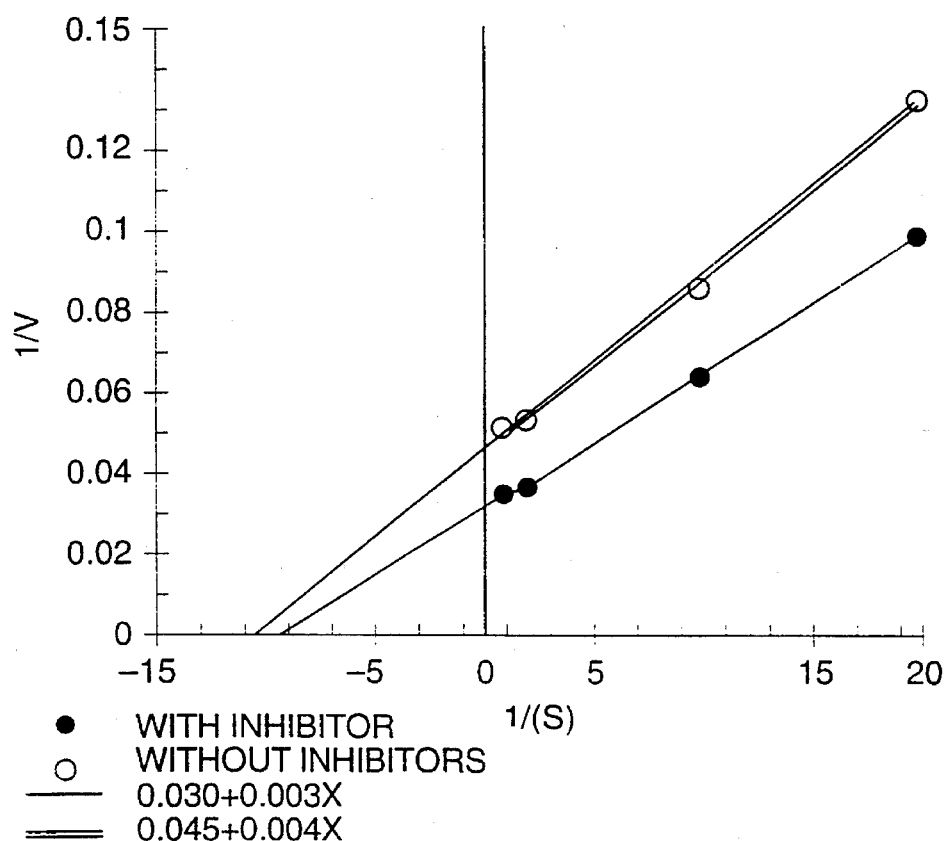
FIG. 7 is a Lineweaver-Burke plot of aldose reductase and intrinsic aldose reductase inhibitor using DL-glyceraldehyde as a substrate.

Although the concentrations of IARI present were not determined, a number of kinetic and in vitro incubation studies were conducted to investigate the mode of inhibition of aldose reductase by the purified IARI. Concentration-dependent inhibition was observed with increasing amounts of IARI (FIG. 6). Kinetic studies using DL-glyceraldehyde as substrate indicated that inhibition did not result from competition of the IARI with substrate (FIG. 7). A mixed type of noncompetitive/uncompetitive inhibition similar to that observed with other aldose reductase inhibitors was observed. IARI inhibition was also not reduced when the concentration of nucleotide cofactor, NADPH, was increased 100-fold. This suggests that the IARI does not compete with NADPH (Table 2).

TABLE 2

Effect of NADPH Concentration of Inhibition by Fixed Concentration of IARI. Control activity is the aldose reductase activity measured in the absence of an IARI.

| NADPH Conc. (µM) | Control Activity* | Activity with IARI* | % Remaining Activity |
|---|---|---|---|
| 10 | 10.37 ± .55 | 8.21 ± .55 | 79.2 |
| 1 | 10.00 ± .44 | 7.47 ± 1.7 | 74.3 |
| 0.1 | 4.90 ± .60 | 3.37 ± 1.2 | 81.0 |

*Activity is expressed as nmols/min/ml NADPH consumed
Numbers represent the mean of four experiments.

Comparisons of inhibition of aldose reductase by IARI with NADH rather than NADPH were also conducted. Under these conditions no difference was observed in the remaining activities obtained with either NADPH or NADH (Table 3).

TABLE 3

Evaluation of the two peaks of IARI activity obtained from silica gel column chromatography on the inhibition of aldose reductase with NADPH and NADH.

| IARI Peak | % Remaining Activity NADPH | % Remaining Activity NADH |
|---|---|---|
| Peak I | 64.8 | 59.5 |
| Peak II | 46.2 | 43.8 |

Numbers represent the mean of two experiments.

These kinetic studies were verified by in vitro inhibition studies with NMR using 3-fluoro-3-deoxy-D-glucose (3FDG) as substrate. To determine the concentration of IARI required, studies were conducted in which the reaction mixture contained 10 mM 3-fluoro-3-deoxy-D-glucose (3-FDG), DL-glyceraldehyde, or D-glucose, 3 mM NADPH, 17.5 mU aldose reductase, 100 mM phosphate buffer, pH 6.2, and 5 mg/ml IARI. Control activity was determined by measuring the activity of aldose reductase without the presence of an IARI. As anticipated, significant differences in the susceptibility to inhibition of aldose reductase by the IARI was observed when different substrates were utilized (Table 4). This is a common effect observed with other noncompetitive/uncompetitive aldose reductase inhibitors and is related to changes in $V_{max}$ (the maximum reaction rate of the enzyme with a particular substrate).

TABLE 4

Effect of Substrate on the Observed Inhibition of IARI on aldose reductase activities for substrates.

| Substrate | Control Activity* | Activity with IARI* | % Remaining Activity |
|---|---|---|---|
| DL-Glyceraldehyde | 35.67 | 4.80 | 13.46 |
| D-Glucose** | 3.62 | 3.53 | 91.27 |
| 3FDG** | 27.46 | 12.36 | 45.00 |

*Activity is expressed as nmols/min/ml NADPH consumed.
**Because of lower Vmax, 5-fold more aldose reductase was utilized for these measurements compared to DL-glyceraldehyde The amount of inhibition of aldose reductase by the IARI with glucose as substrate was difficult to assess because of the low $V_{max}$ of the enzyme with this substrate. Nevertheless, a relationship between inhibition by fixed amounts of the IARI and the concentration of enzyme present was observed with inhibition increasing slightly (7%). The production of 3FDS (3-fluorodeoxy-sorbitol) by aldose reductase was also measured using NMR. The experimental conditions for the NMR studies are presented in Table 5.

TABLE 5

Experimental Conditions for in vitro NMR Studies.

| | with IARI | without IARI |
|---|---|---|
| Aldose Reductase (1.75 U/ml) | 2000 µl | 2000 µl |
| 0.5M Tris/HCl, pH 7.5 | 700 µl | 700 µl |
| 20 mM NADPH | 700 µl | 700 µl |
| 300 mM 3FDG | 500 µl | 500 µl |
| ARI (100 mg/ml) | 700 µl | 0 µl |
| 100 mM Glucose-6-phosphate (G6P)* | 700 µl | 700 µl |
| G6P dehydrogenase (20 U/ml)* | 700 µl | 700 µl |
| Water | 0 µl | 700 µl |
| Total Volume | 6000 µl | 6000 µl |

*D-Glucose-6-phosphate and its dehydrogenase were added for recycling the NADPH during the assay.

Figure 8A:
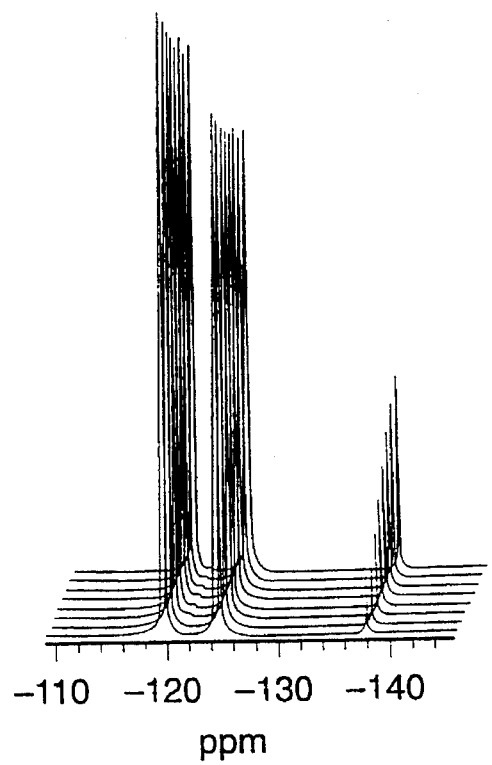
FIG. 8(A) illustrates the production of 3FDS (3-fluoro-deoxy-sorbitol) at successive time intervals in the absence of intrinsic aldose reductase inhibitor. The peaks at approximately 120 and 125 ppm represent 3-fluoro-3-deoxy-D-glucose (3FDG) anomers while the single peak at approximately 138 ppm represents 3FDS.
Figure 8B:
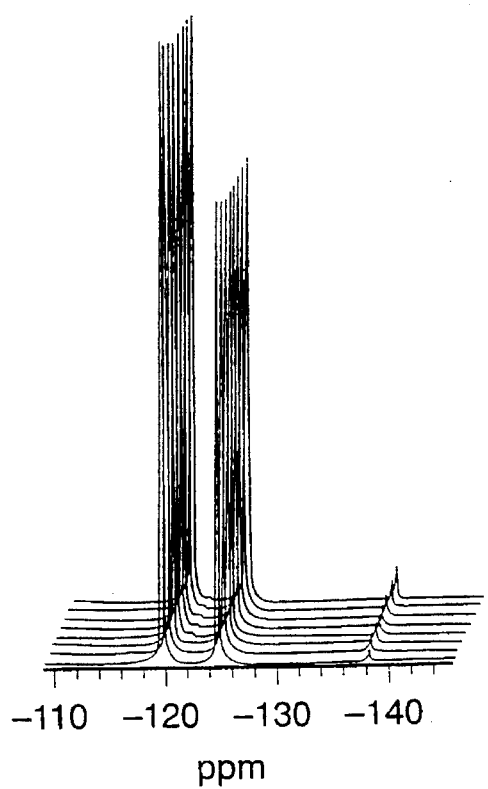
FIG. 8(B) illustrates the production of 3FDS (3-fluoro-deoxy-sorbitol) at successive time intervals in the presence of intrinsic aldose reductase inhibitor. The peaks at approximately 120 and 125 ppm represent 3-fluoro-3-deoxy-D-glucose (3FDG) anomers while the single peak at approximately 138 ppm represents 3FDS.

FIG. 8(A) illustrates the production of 3FDS (3-fluoro-deoxy-sorbitol) in the absence of intrinsic aldose reductase inhibitor, while FIG. 8(B) illustrates the production of 3FDS in the presence of intrinsic aldose reductase inhibitor. The peaks at approximately 120 and 125 ppm represent 3-fluoro-3-deoxy-D-glucose (3FDG) anomers while the single peak at approximately 138 ppm represents 3FDS. Clearly, the production 3FDS is reduced in the presence of IARI indicating inhibition of aldose reductase.

Figure 9:
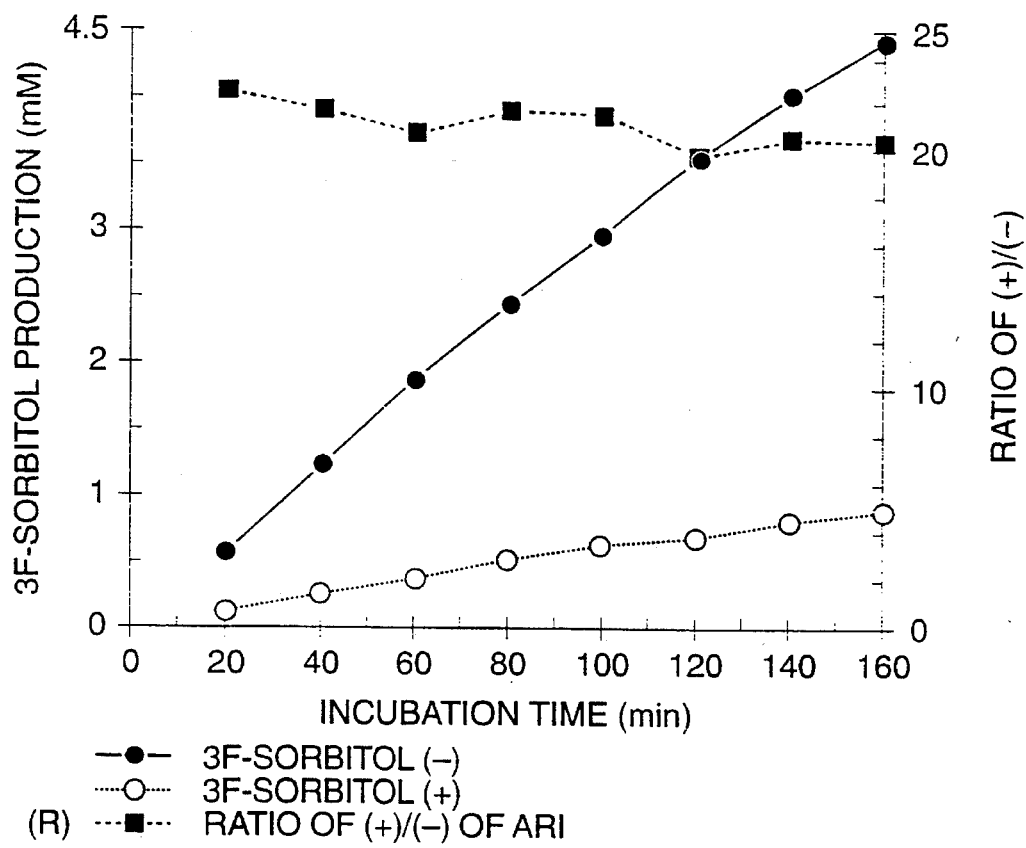
FIG. 9 is a comparison of the production of 3FDS with and without intrinsic aldose reductase inhibitor over time. The black squares represent the ratio of 3FDS production with and without an intrinsic aldose reductase inhibitor (ARI).

After initiating the reaction by the addition of NADPH to the reaction mixture, 3-fluoro-3-deoxy-sorbitol (3FDS) production by aldose reductase increased linearly with time (FIG. 9). The rate of 3-fluoro-3-deoxy-sorbitol (3FDS) production was reduced in the presence of the IARI.

Comparison of 3FDS production with and without inhibitor over time (FIG. 9) resulted in a constant number of 20%. This indicates that the observed inhibition by IARI was not due to irreversible inactivation of the enzyme because the inhibition percentage remained constant.

Effect of IARI on Other Pyrimidine Nucleotide-Dependent Enzymes

The selectivity of this IARI for other pyrimidine nucleotide dependent oxidoreductases such as sorbitol dehydrogenase, 3.α-hydroxysteroid dehydrogenase, glutathione reductase and glucose 6-phosphate dehydrogenase was also assessed. These enzymes were evaluated under the conditions summarized below:

| Aldose Reductase | |
|---|---|
| 10 mM | DL-Glyceraldehyde |
| 0.3 mM | NADPH |
| 100 mM | Phosphate buffer, pH 6.2 |
| 20 µl | sample (1.5 U/ml) |
| 50 µl | IARI |

| α-Hydroxysteroid Dehydrogenase | | | |
|---|---|---|---|
| reductase activity | | dehydrogenase activity | |
| 0.2 mM | Androstenedione | 0.2 mM | Androsterone |
| 0.3 mM | NADH | 0.3 mM | NAD+ |
| 100 mM | BisTris, pH 7.5 | 100 mM | BisTris, pH 7.5 |
| 20 µl | Sample (1 U/ml) | 20 µl | Sample (1 U/ml) |
| 50 µl | IARI | 50 µl | IARI |

| Sorbitol Dehydrogenase | | | |
|---|---|---|---|
| reductase activity | | dehydrogenase activity | |
| 10 mM | D-Fructose | 10 mM | Sorbitol |
| 0.3 mM | NADH | 0.3 mM | NAD+ |
| 100 mM | BisTris, pH 7.5 | 100 mM | BisTris, pH 7.5 |
| 100 µl | Sample (0.2 U/ml) | 100 µl | Sample (0.2 U/ml) |
| 50 µl | IARI | 50 µl | IARI |

| Glutathione Reductase | | Glucose 6-Phosphate Dehydrogenase | |
|---|---|---|---|
| 10 mM | GSSG | 100 mM | Glucose-6-phosphate |
| 0.3 mM | NADPH | 0.3 mM | NADP+ |
| 100 mM | Phosphate, pH 6.2 | 100 mM | BisTris, pH 1.5 |
| 50 µl | Sample (0.2 U/ml) | 50 µl | Sample (0.2 U/ml) |
| 50 µl | IARI | 50 µl | IARI |

The effect of the IARI, obtained as the colorless peak from silica gel column using acetonitrile:water:TFA (90:10:0.5 v/v), on these enzymes is summarized below in Table 6.

TABLE 6

Effects of IARI on Other Enzymes

| Enzyme (Oxidoreductase) | Origin | % Remaining Activity[3] | |
|---|---|---|---|
| | | Reductase | Dehydrogenase |
| NADP(H)-dependent Aldose reductase | — | 65.2 | — |
| Glucose 6-phosphate dehydrogenase | Yeast[1] | — | 104.0 |
| Glutathione reductase NAD(H)-dependent | Bakers Yeast[2] | 96.5 | — |
| Sorbitol dehydrogenase | Sheep liver[2] | — | 106.0 |
| 3-α-Hydroxysteroid dehydrogenase | *Pseudomonas testosterium*[2] | 110.7 | 95.4 |

[1]Boehringer Mannheim Corp., Indianapolis, Indiana.
[2]Sigma Chemical Co., St. Louis, Missouri.
[3]Values represent the mean of two experiments.

EXAMPLE 2

HPLC Purification of Intrinsic Aldose Reductase Inhibitors

One hundred rat kidneys (about 35 grams), obtained from Pel-Freez (Rogers, AR) were homogenized with 70 ml of water using a Waring Blender. The homogenate was centrifuged at 12,000–13,000 rpm for 90 minutes, and the resulting supernatant was subjected to dialysis against 500 ml of water, using a Spectra/Pore (Spectrum, Houston, Tex.) dialysis membrane with a molecular weight cutoff of 1000, overnight (for at least 18 hours). After dialysis, the components which came out of the cellulose membrane were frozen and concentrated by lyophilization. The lyophilized powder was dissolved in a minimum volume of water, centrifuged at 4,000 rpm for 15 minutes, and the supernatant was applied to a Sephadex G-10 (2.4×72 cm) column from Pharmacia-LKB Biotechnology Co. (Piscataway, N.J.). Elution was performed with water, and fractions were collected at 100 drops/tube. Two inhibitor activity peaks were found in the elution. The inhibitor active fractions were collected separately, and both peaks were applied to a CM-cellulose (2.4×25 cm) column which was obtained from Sigma Chemical Company (St. Louis, Mo.). All the inhibitor activities passed through these columns and were lyophilized.

Figure 10:
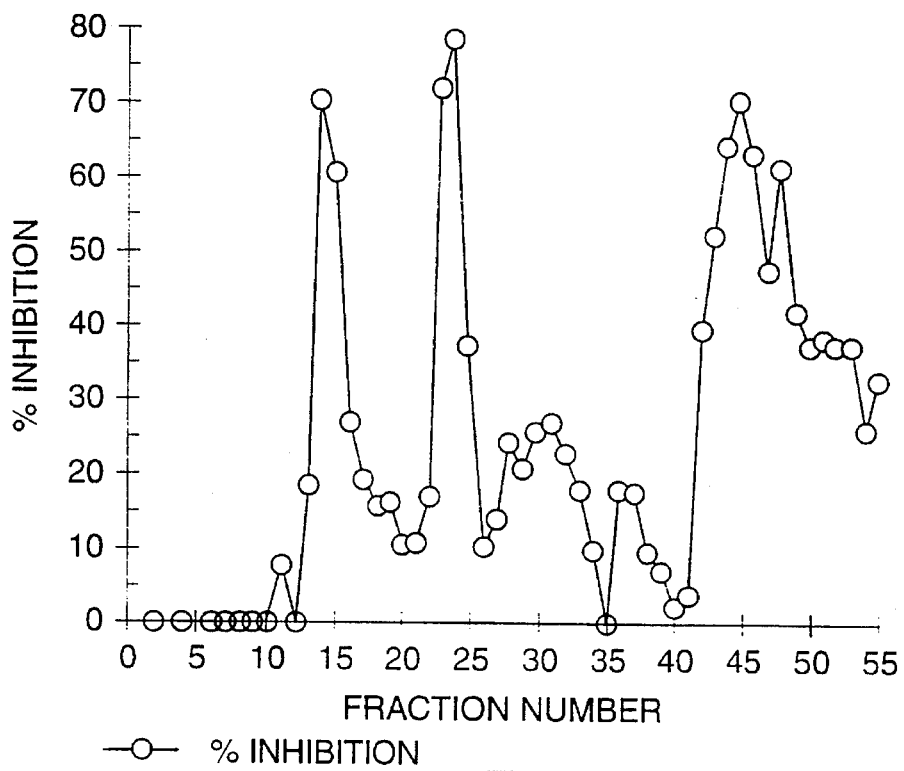
FIG. 10 is a reverse-phase chromatographic elution profile of intrinsic aldose reductase inhibitor obtained from a C-18 column (300 Å, 4.6×250 mm, Vydac, Hesperia, Calif.) eluted with a 0–50% acetonitrile gradient in 0.5% trifluoroacetic acid. Intrinsic aldose reductase inhibitor activity was found in 3 peaks corresponding to fractions 14 through 15, 23 through 24, and fraction 45 respectively.
Figure 11:
FIG. 11 illustrates the thin layer chromatographic separation of fractions 14, 15, 23, and 45 obtained from the reverse phase chromatography of FIG. 10. The thin layer chromatographic plate was eluted with butanol:acetic acid:water (7:3:2 v/v) and stained with ninhydrin.

The concentrated higher fractions were further purified by reverse phase chromatography using a C-18 column (300 Å, 4.6×250 mm, Vydac, Hesperia, Calif.) using water with 0.5% trifluoroacetic acid and applying a 0 to 50% acetonitrile gradient. 1 ml fractions were collected. The IARI peaks corresponded to fractions 14–15; 23–24 and 45 (FIG. 10.) Peaks 14–15 and 45 stained with ninhydrin (FIG. 11).

Thin layer chromatography (TLC) of crude kidney extracts (ke) as well as of purified intrisic aldose reduction inhibitors as described above, was conducted on silica plates (20×20 cm, 250 µm thick, Whatman, KG silica gel, Sigma, St. Louis, Mo.), using acetic acid:ethanol:water as the eluent. The ratio of solvents in the mixture was 7:1:2 v/v. This chromatographic system separated the crude rate and human kidney extracts into approximately 11 different bands. All detections systems were tested with positive controls to assure the effectiveness of the reagents. Both human and rat kidney extracts gave similar results. The results for HPLC purified human kidney extract are presented in Table 7. TLC indicated positive results for $UV_{254}$ and anisaldehyde with very strong staining for ninhydrin. The $UV_{254}$ and ninhydrin results indicate a polypeptide component for the intrinsic aldose reductase inhibitors. No other known aldose reductase inhibitor stains positive for ninhydrin.

TABLE 7

TLC results for HPLC purified human kidney extract.

| Treatment | Detects | Results |
|---|---|---|
| $UV_{254}$ | | 2 bands at $R_f$ 0.59 and 0.69 |
| Anisaldehyde | carbohydrates | 1 band at $R_f$ 0.643 |
| Ninhydrin | amino acids, amino sugars phosphatides | 9 bands at $R_f$ 0.0027, 0.150, 0.239, 0.308, 0.344, 0.376, 0.445, 0.506, 0.589, 0.643 |
| 2'-7' dichlorofluorescein | lipids and lipophiles | negative |
| Fluorescein | conjugated systems | negative |
| Bromcresol green | carboxylic acids | negative |
| $SbCl_3$ in $CHCl_3$ | steroids, vitamins, lipids, carotenoids | negative |
| 2,4-dinitrophenyl hydrazine | ketones, aldehydes | negative |
| $FeCl_3$ (1% Ag) | phenols, enols | negative |
| Dragendorff's reagent* | alkaloids, organic bases | negative |

*Sigma Chemical Co., St. Louis, MO.

To increase the purity and concentration of inhibitor, the purified human kidney extract was fractionated through a silica gel column (vol 350 ml) using an ethanol:acetic acid:water mixture (7:1:2 v/v) as the eluent.

Figure 14:
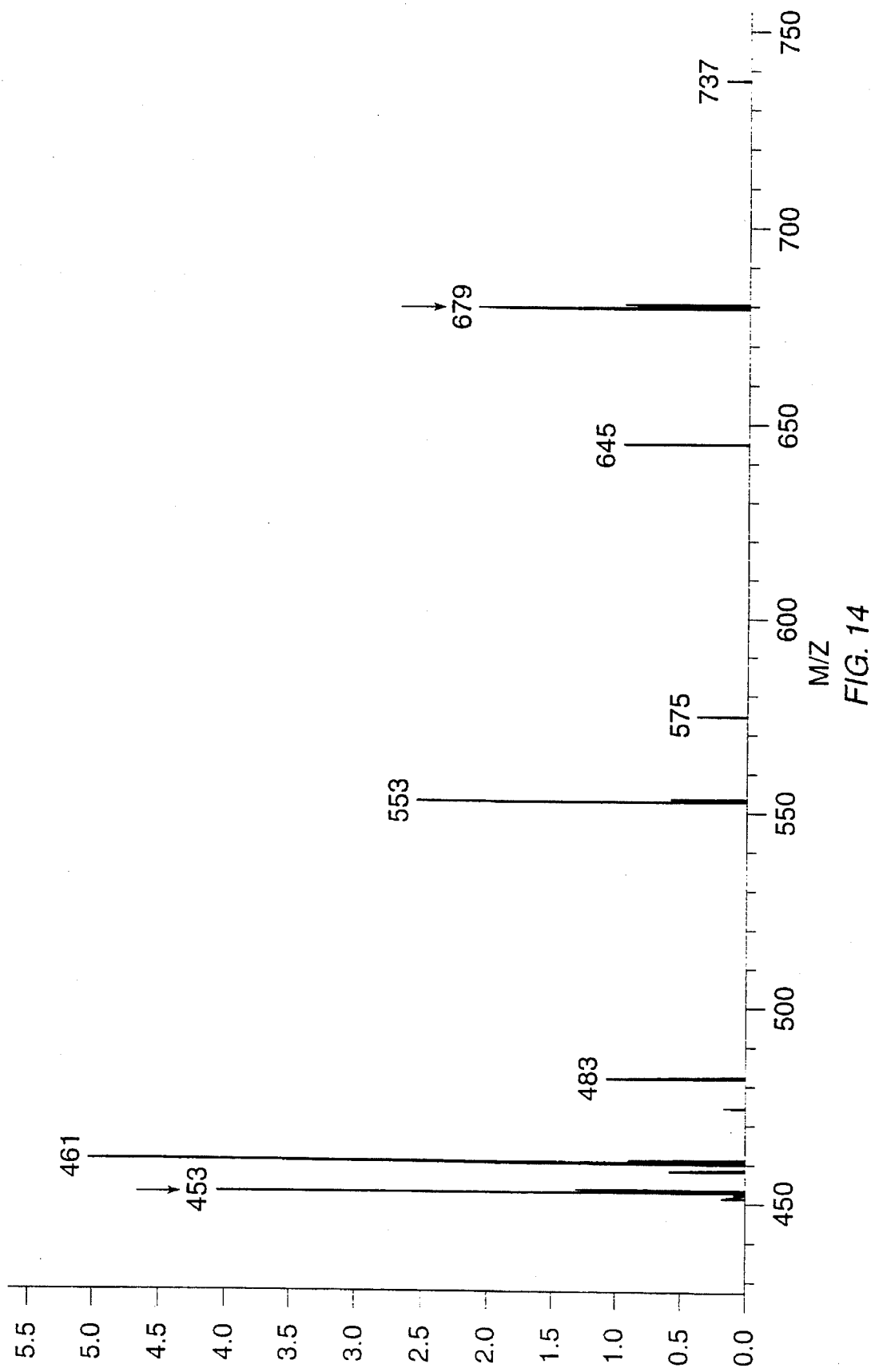
FIG. 14 represents a fast atom bombardment spectrum for IARI-containing fractions purified by reverse-phase HPLC and then fractionated on a silica gel column. The FAB spectrum shows two peaks at masses of 453 and 679.

The resulting fractions were assayed for aldose reductase inhibitory activity as described in Example 1. A fast atom bombardment (FAB) mass spectrometry was obtained for the fraction containing the highest inhibitory activity (greater than 91%). The FAB spectrum (FIG. 14) shows two peaks at masses of 453 and 679.

EXAMPLE 3

Rapid Isolation and Purification of IARI

A human kidney was homogenized in a blender using 2 ml of ethanol per gram of tissue. The homogenate was centrifuged at 8000 rpm for 45 minutes and the supernatant was then filtered through glasswool. The supernatant was then concentrated to dryness by evaporation in a rotary evaporator and re-dissolved in 20 ml of water. This step yielded a solution with a yellowish color.

The supernatant was then fractionated using reverse phase HPLC on a C-18 (RP C-18 90 Å pharmaceutical column, 9×250 mm, Vydac, Hesperia, Calif.) on Pharmacia HPLC system (Pharmacia-LKB Biotechnology Co., Piscataway, N.J.). Solvent A was water and solvent B was 50% methanol. The inhibitor was eluted using the following gradient:

0–10 min. 5% B; 10–35 min 5%–100% B; 45–50 min 100%–5% B; This gradient provides a 10 minute equilibration at 2.5% methanol followed by a 25 minute linear gradient going from 2.5% to 50% methanol.

This HPLC system was very efficient in fractionating the rat and human kidney extracts into several distinct peaks (see FIG. 12). The elution profiles are highly consistent yielding the same results both between HPLC runs of extract from similar tissues and when comparing rat and human extracts for aldose reductase inhibitory activity (data not shown). One inhibitory peak eluted early in the gradient at approximately 4% methanol and a second inhibitory peak eluted later in the gradient at 50% methanol.

The early eluting peak actually corresponds to the void volume of the C-18 column. The fractions corresponding to this peak (e.g. fractions 6–8 in FIG. 12) were collected, pooled, and fractionated using a C-8 column (pH stable RP C-8 column, Vydak, Hesperia, Calif.) run isocratic in water containing 2.5% methanol at a rate of 0.3 ml/min collecting fractions at 0.3 minute intervals. The elution profile of the C-8 column, shown in FIG. 13, reveals a profile with a single dominant peak. Fractions selected from this peak show aldose reductase inhibitory activity in excess of 75%. The profiles produced by both the C-18 column and the C-8 column are highly reproducible from sample to sample regardless of the whether the material is derived from human or rats. This protocol thus provides a rapid, highly reproducible method of isolating a composition containing highly active intrinsic aldose reductase inhibitors.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated aldose reductase inhibitor obtained from mammalian cells selected from the group consisting of kidney cells, lens cells and thyroid cells, said inhibitor being obtained by the steps of:

homogenizing said cells in ethanol, separating a supernatant, evaporating the supernatant to obtain a dried supernatant and then redissolving the dried supernatant in water, fractionating the redissolveddried supernatant on a C-18 reverse phase column by eluting with methanol using a linear gradient of 2.5% methanol to 50% methanol over 25 minutes to obtain inhibitor containing fractions, and pooling the inhibitor containing fractions containing approximately 4% methanol;

and wherein said inhibitor stains positive with ninhydrin and anisaldeyde, stains negative with fluorescein, 2'-7'-dichlorofluorescein, bromocresol green, $SbCl_3$ in $CHCl_3$, 2,4-dinitrophenyl hydrazine, $FeCl_3$ (1% Ag), and Dragendorff's reagent, and has a molecular weight of less than 1,000 daltons.

2. The aldose reductase inhibitor of claim 1 wherein said inhibitor is obtained in a single activity peak when the pooled fractions containing inhibitor from the C-18 reverse phase column are run isocratically on a C-8 reverse phase column in 2.5% methanol.

3. The aldose reductase inhibitor of claim 1, wherein said inhibitor has been purified to at least 10% w/w.

4. A method for inhibiting aldose reductase activity in mammalian cells in vitro, comprising adding an inhibitory effective amount of the aldose reductase inhibitor of claim 1 to the mammalian cells.

5. The method of claim 4, wherein said mammalian cells are human cells.

* * * * *